United States Patent
Kayan

(10) Patent No.: US 9,402,623 B2
(45) Date of Patent: Aug. 2, 2016

(54) SURGICAL FASTENERS

(71) Applicant: Covidien LP, Mansfield, MA (US)

(72) Inventor: Helmut Kayan, Redwood City, CA (US)

(73) Assignee: Covidien LP, Mansfield, MA (US)

(\*) Notice: Subject to any disclaimer, the term of this patent is extended or adjusted under 35 U.S.C. 154(b) by 0 days.

(21) Appl. No.: 14/321,093

(22) Filed: Jul. 1, 2014

(65) Prior Publication Data

US 2014/0316446 A1    Oct. 23, 2014

Related U.S. Application Data

(63) Continuation of application No. 10/493,509, filed as application No. PCT/US02/33984 on Oct. 22, 2002, now Pat. No. 8,777,969.

(60) Provisional application No. 60/347,846, filed on Oct. 23, 2001.

(51) Int. Cl.
*A61B 17/064* (2006.01)
*A61B 17/068* (2006.01)

(52) U.S. Cl.
CPC ............ *A61B 17/064* (2013.01); *A61B 17/068* (2013.01); *A61B 2017/0641* (2013.01); *A61B 2017/0647* (2013.01); *A61B 2017/0648* (2013.01); *A61B 2017/0649* (2013.01)

(58) Field of Classification Search
CPC . A61B 17/064; A61B 17/0642; A61B 17/057

USPC ......... 606/65, 72, 75, 80, 139, 151, 219, 220, 606/279, 291, 304, 312; 411/457; 227/137
See application file for complete search history.

(56) References Cited

U.S. PATENT DOCUMENTS

| | | |
|---|---|---|
| 1,131,085 A | 3/1915 | Reilly |
| 2,103,944 A | 12/1937 | Gullborg |
| 3,364,200 A | 1/1968 | Ashton et al. |
| 3,379,231 A | 4/1968 | Gallo |
| 3,672,058 A | 6/1972 | Nikoghossian |
| 3,673,912 A | 7/1972 | Herr |
| 3,939,068 A | 2/1976 | Wendt et al. |
| 3,948,666 A | 4/1976 | Kitanishi et al. |

(Continued)

FOREIGN PATENT DOCUMENTS

| | | |
|---|---|---|
| DE | 10300787 A1 | 9/2004 |
| EP | 0374088 A1 | 6/1990 |

(Continued)

OTHER PUBLICATIONS

Extended European Search Report corresponding to EP No. 10 01 2659.8, completed Dec. 21, 2010 and mailed Jan. 3, 2011; 3 pages.

(Continued)

*Primary Examiner* — Vy Bui

(57) ABSTRACT

Surgical fasteners, including tacks are disclosed for fastening a surgical mesh to underlying tissue during surgical procedures to repair body tissue, such as in hernia repair. Such tacks can include a head, a elongated body portion having a distal end and a proximal end, and an anchoring element on an outer surface of the body portion for inhibiting the removal of the tack from the mesh and body tissue.

4 Claims, 3 Drawing Sheets

(56) References Cited

U.S. PATENT DOCUMENTS

| | | | |
|---|---|---|---|
| 4,006,660 A | 2/1977 | Yamamoto et al. |
| 4,064,062 A | 12/1977 | Yurko |
| 4,142,293 A | 3/1979 | Tieche |
| 4,166,800 A | 9/1979 | Fong |
| 4,282,236 A | 8/1981 | Broom |
| 4,416,698 A | 11/1983 | McCorsley, III |
| 4,429,599 A | 2/1984 | La Sante, Sr. |
| 4,454,875 A | 6/1984 | Pratt et al. |
| 4,548,202 A | 10/1985 | Duncan |
| 4,570,623 A | 2/1986 | Ellison et al. |
| 4,592,346 A | 6/1986 | Jurgutis |
| 4,626,253 A | 12/1986 | Broadnax, Jr. |
| 4,756,653 A | 7/1988 | Berger |
| 4,776,329 A | 10/1988 | Treharne |
| 4,994,073 A | 2/1991 | Green |
| 5,053,036 A | 10/1991 | Perren et al. |
| 5,057,334 A | 10/1991 | Vail |
| 5,162,430 A | 11/1992 | Rhee et al. |
| 5,203,864 A * | 4/1993 | Phillips ............. A61B 17/064 227/137 |
| 5,236,431 A * | 8/1993 | Gogolewski ....... A61B 17/0642 606/139 |
| 5,236,563 A | 8/1993 | Loh |
| 5,324,775 A | 6/1994 | Rhee et al. |
| 5,410,016 A | 4/1995 | Hubbell et al. |
| 5,417,712 A | 5/1995 | Whittaker et al. |
| 5,454,814 A | 10/1995 | Comte |
| 5,478,354 A * | 12/1995 | Tovey ............... A61B 17/0057 411/457 |
| 5,484,913 A | 1/1996 | Stilwell et al. |
| 5,514,379 A | 5/1996 | Weissleder et al. |
| 5,543,441 A | 8/1996 | Rhee et al. |
| 5,550,187 A | 8/1996 | Rhee et al. |
| 5,599,131 A | 2/1997 | Julen et al. |
| 5,720,766 A | 2/1998 | Zang et al. |
| 5,743,914 A | 4/1998 | Skiba |
| 5,752,974 A | 5/1998 | Rhee et al. |
| 5,819,350 A | 10/1998 | Wang |
| 5,827,298 A * | 10/1998 | Hart .................... A61B 17/064 606/139 |
| 5,874,500 A | 2/1999 | Rhee et al. |
| 5,971,985 A * | 10/1999 | Carchidi ............ A61B 17/0642 606/312 |
| 5,984,927 A * | 11/1999 | Wenstrom et al. ............ 606/329 |
| 6,036,701 A | 3/2000 | Rosenman |
| 6,093,557 A | 7/2000 | Pui et al. |
| 6,152,943 A | 11/2000 | Sawhney |
| 6,156,677 A | 12/2000 | Brown Reed et al. |
| 6,165,201 A | 12/2000 | Sawhney et al. |
| 6,179,862 B1 | 1/2001 | Sawhney |
| 6,187,009 B1 | 2/2001 | Herzog et al. |
| 6,269,716 B1 | 8/2001 | Amis |
| 6,277,130 B1 | 8/2001 | Shadduck |
| 6,306,136 B1 | 10/2001 | Baccelli |
| 6,309,569 B1 | 10/2001 | Farrar et al. |
| 6,345,925 B1 | 2/2002 | Coleman |
| 6,399,362 B1 | 6/2002 | Pui et al. |
| 6,402,757 B1 | 6/2002 | Moore, III et al. |
| 6,500,777 B1 | 12/2002 | Wiseman et al. |
| 6,514,534 B1 | 2/2003 | Sawhney |
| 6,551,343 B1 * | 4/2003 | Tormala et al. ............ 606/213 |
| 6,566,406 B1 | 5/2003 | Pathak et al. |
| 6,590,095 B1 | 7/2003 | Schleicher et al. |
| 6,605,294 B2 | 8/2003 | Sawhney |
| 6,627,749 B1 | 9/2003 | Kumar |
| 6,656,200 B2 | 12/2003 | Li et al. |
| 6,673,093 B1 | 1/2004 | Sawhney |
| 6,703,047 B2 | 3/2004 | Sawhney et al. |
| 6,746,869 B2 | 6/2004 | Pui et al. |
| 6,764,720 B2 | 7/2004 | Pui et al. |
| 6,818,018 B1 | 11/2004 | Sawhney |
| 6,929,661 B2 | 8/2005 | Bolduc et al. |
| 7,009,034 B2 | 3/2006 | Pathak et al. |
| 7,128,754 B2 | 10/2006 | Bolduc |
| 7,247,338 B2 | 7/2007 | Pui et al. |
| 7,279,322 B2 | 10/2007 | Pui et al. |
| 7,347,850 B2 | 3/2008 | Sawhney |
| 7,498,063 B2 | 3/2009 | Pui et al. |
| 7,595,392 B2 | 9/2009 | Kumar et al. |
| 7,611,494 B2 | 11/2009 | Campbell et al. |
| 7,649,089 B2 | 1/2010 | Kumar et al. |
| 7,662,801 B2 | 2/2010 | Kumar et al. |
| 7,951,248 B1 | 5/2011 | Fallis et al. |
| 8,033,483 B2 | 10/2011 | Fortier et al. |
| 8,075,570 B2 | 12/2011 | Bolduc et al. |
| 8,152,777 B2 | 4/2012 | Campbell et al. |
| 8,231,639 B2 | 7/2012 | Bolduc et al. |
| 2002/0086990 A1 | 7/2002 | Kumar et al. |
| 2003/0078209 A1 | 4/2003 | Schmidt |
| 2003/0114839 A1 | 6/2003 | Looper et al. |
| 2004/0111089 A1 | 6/2004 | Stevens et al. |
| 2004/0181222 A1 | 9/2004 | Culbert et al. |
| 2004/0243139 A1 | 12/2004 | Lewis et al. |
| 2005/0131225 A1 | 6/2005 | Kumar et al. |
| 2005/0154093 A1 | 7/2005 | Kwon et al. |
| 2006/0008505 A1 | 1/2006 | Brandon |
| 2006/0093672 A1 | 5/2006 | Kumar et al. |
| 2006/0121266 A1 | 6/2006 | Fandel et al. |
| 2007/0054880 A1 | 3/2007 | Saferstein et al. |
| 2007/0213522 A1 | 9/2007 | Harris et al. |
| 2007/0237741 A1 | 10/2007 | Figuly et al. |
| 2007/0237742 A1 | 10/2007 | Figuly et al. |
| 2008/0164440 A1 | 7/2008 | Maase et al. |
| 2008/0194805 A1 | 8/2008 | Vignon et al. |
| 2008/0214695 A1 | 9/2008 | Pathak et al. |
| 2008/0243106 A1 | 10/2008 | Coe et al. |
| 2009/0220560 A1 | 9/2009 | Wan et al. |
| 2009/0263441 A1 | 10/2009 | McKay |
| 2010/0065660 A1 | 3/2010 | Hull et al. |
| 2010/0096481 A1 | 4/2010 | Hull et al. |
| 2010/0203151 A1 | 8/2010 | Hiraoka |
| 2011/0082427 A1 | 4/2011 | Golzarian et al. |
| 2011/0089375 A1 | 4/2011 | Chan et al. |
| 2011/0293690 A1 | 12/2011 | Griffin et al. |
| 2012/0156289 A1 | 6/2012 | Blaskovich et al. |
| 2015/0133970 A1 | 5/2015 | Ranucci et al. |
| 2015/0133971 A1 | 5/2015 | Ranucci et al. |
| 2015/0133972 A1 | 5/2015 | Ranucci et al. |

FOREIGN PATENT DOCUMENTS

| | | |
|---|---|---|
| EP | 0834280 A1 | 4/1998 |
| EP | 1025803 A1 | 8/2000 |
| EP | 1273272 A2 | 1/2003 |
| EP | 1990013 A1 | 11/2008 |
| EP | 2399538 A2 | 12/2011 |
| JP | 09149906 | 6/1997 |
| WO | 9606565 A1 | 3/1996 |
| WO | 0030552 A1 | 6/2000 |
| WO | 0137741 A1 | 5/2001 |
| WO | 0156533 A2 | 8/2001 |
| WO | 02/34140 A2 | 5/2002 |
| WO | 03/034925 A2 | 5/2003 |
| WO | 03/103507 A2 | 12/2003 |
| WO | 2004/112841 A2 | 12/2004 |
| WO | 2009/039506 A1 | 3/2009 |
| WO | 2013/046115 A1 | 4/2013 |

OTHER PUBLICATIONS

Extended European Search Report corresponding to EP No. 10 01 2646.5, completed Feb. 11, 2011 and mailed Feb. 22, 2011; 10 pages.
Extended European Search Report corresponding to EP No. 11 25 0549.0, completed Sep. 9, 2013 and mailed Sep. 17, 2013; 9 pages.
Extended European Search Report corresponding to EP 14 15 9394.7, completed Apr. 16, 2014 and mailed Apr. 29, 2014; 8 pages.
Extended European Search Report corresponding to counterpart application EP 14 19 7885.8 dated Mar. 30, 2015; 9pp.
Extended European Search Report corresponding to counterpart application EP 14 18 1900.3 dated Apr. 9, 2015; 7pp.
International Search Report mailed Apr. 11, 2003 in corresponding International Application No. PCT/US02/33984, 6 Pages.

* cited by examiner

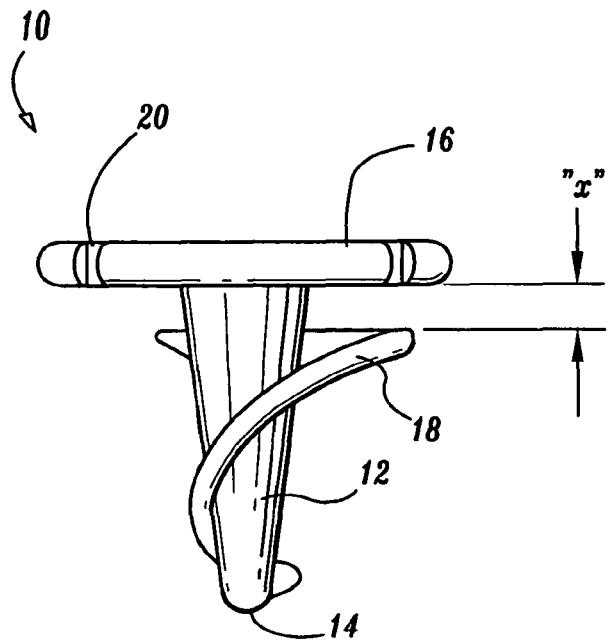
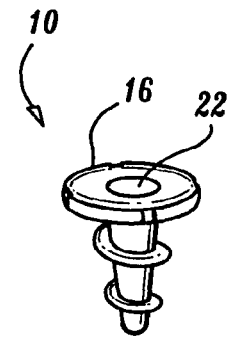
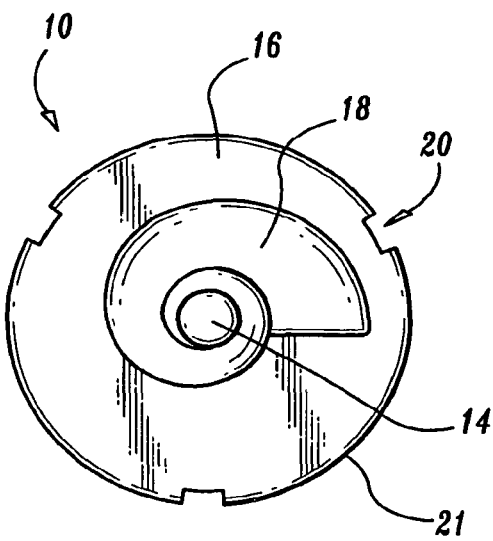
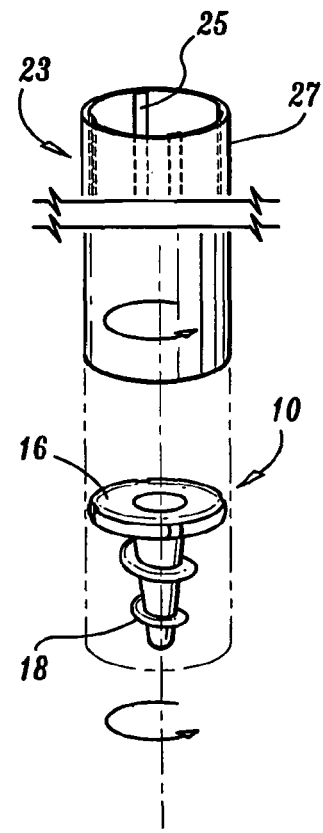
FIG. 1
FIG. 3
FIG. 2
FIG. 4

SURGICAL FASTENERS

CROSS-REFERENCE TO RELATED APPLICATION

This application is a continuation of U.S. patent application Ser. No. 10/493,509 filed Apr. 21, 2004, which is a National Stage Application of PCT/US2002/033984 filed Oct. 22, 2002 under 35 USC §371 (a), which claims priority of U.S. Provisional Patent Application Ser. No. 60/347,846 filed Oct. 23, 2001 the entire contents of which are hereby incorporated by reference.

BACKGROUND

1. Technical Field

The present disclosure relates generally to surgical fasteners for securing objects to body tissue and, more particularly, to surgical tacks for fastening a surgical mesh to underlying tissue during surgical procedures to repair body tissue, such as in hernia repair procedures.

2. Background of Related Art

In various surgical procedures, fasteners in the form of staples or the like are employed for holding tissue portions together to facilitate healing of a wound or incision. Other tissue fastening devices have been proposed and differ from staples per se in that these other devices may have a plurality of components and do not have to be clinched in the manner used to set a staple. For example, such fastening devices require access to both sides of a tissue site since they typically include an upper section having a crown and legs and a lower receiver, wherein the lower receiver engages and locks the legs of the upper section.

Although many of the above-discussed types of tissue fastening devices and techniques are satisfactory in various applications, there is a need to provide improved fastening devices which are relatively easier to apply and relatively difficult to remove. In particular, there is a need for surgical fastening devices which do not require a second separate piece or receiver to lock, form or maintain the fastener in place in tissue, which can be applied and secured from one side of a tissue site, most desirably in an endoscopic or open surgical procedure, and which overcome the disadvantages associated with conventional surgical staples.

SUMMARY

The present disclosure relates to surgical tacks primarily for fastening a surgical mesh to underlying tissue during surgical procedures to repair body tissue, such as in hernia repair procedures. In one aspect of the present disclosure, a tack for use in performing the surgical procedure includes an elongated body portion having a distal end and a proximal end, a head integrally coupled to the proximal end of the body portion and having a proximal surface and a distal surface, and an anchoring element provided on an outer surface of the body portion for inhibiting removal of the tack from body tissue.

It is envisioned that the anchoring element is a helical thread extending at least along a portion of the length of the body portion. Preferably, the body portion is conical, although, the body portion can be tapered such that a girth of the body portion is smaller at its distal end than at its proximal end.

The head preferably has a diameter which is larger than a diameter of the proximal end of the body portion. It is contemplated that the head includes a stackable feature, wherein the stackable feature preferably is a recess formed in the proximal surface of the head. The distal end of the body portion is atraumatic, preferably rounded. It is envisioned that the distal end of the body portion and the recess are configured and dimensioned such that the distal end of a similar tack can be seated within the recess.

In one embodiment, the helical thread terminates at a distance spaced from the distal surface of the head. In the same or another embodiment, the helical thread commences at a distance spaced from the distal end of the body portion.

In an embodiment, the tack can include at least one resilient prong extending from the outer surface of the body portion. The at least one resilient prong preferably is disposed between the distal end of the body portion and the helical thread. Preferably, the at least one resilient prong extends from the outer surface of the body portion from a location distally of the head.

In an embodiment, the anchoring element can include at least one resilient prong extending from an outer surface of the body portion, wherein the at least one prong has an unbiased orientation which is substantially orthogonal to a longitudinal axis of the body portion. It is contemplated that the at least one resilient prong is capable of being biased solely in a direction towards the head. Preferably, a first set of resilient prongs is provided near the distal end of the body portion and a second set of resilient prongs is provided on the body portion, proximally of the first set. It is envisioned that each set of resilient prongs includes two pair of diametrically opposed prongs. In another embodiment, the anchoring element includes at least one barb formed along on an outer surface of the body portion, preferably, at least a pair of barbs is formed along a single side of the body portion. The two pair of diametrically opposed barbs are provided near either the distal end of the body portion or near the proximal end of the body portion.

It is envisioned that the head of the tack has a rim having at least one notch formed therein.

It is contemplated that the tack is made from a biocompatible material.

In another aspect to of the present disclosure, the tack can include a backing member, at least two legs depending distally from the backing member, wherein the legs are substantially orthogonal to the backing member and are oriented in substantially the same direction as one another, and an anchoring element provided on an outer surface of each leg for inhibiting the removal of the tack from body tissue.

Preferably, the anchoring element is at least one barb extending from the outer surface of each leg. It is contemplated that each barb is oriented in a proximal direction. One of the barbs is provided near the distal end of each leg and another of the barbs is provided near a proximal end of each leg.

The backing member preferably includes at least two recesses formed in a proximal surface thereof, each recess being axially aligned with a longitudinal axis of a respective leg. The backing member preferably is elongated or annular. In one embodiment, it is envisioned that the backing member is triangular and includes a leg depending from each respective corner of the backing member. In an embodiment, it is envisioned that the anchoring elements are barbs extending from the outer surface of each leg.

It is further envisioned that the backing member is elongated and that a leg depends from each respective end of the elongated member.

It is envisioned that the tack is fabricated from a bioabsorbable material.

These and other features and advantages of the present disclosure will become apparent from consideration of the following description taken in conjunction with the accompanying drawings.

BRIEF DESCRIPTION OF THE DRAWINGS

The accompanying drawings, which are incorporated and constitute a part of this specification, illustrate embodiments of the disclosure and, together with a general description of the disclosure given above, and the detailed description of the embodiments given below, serve to explain the principles of the disclosure.

FIG. 1 is a side elevational view of a fastening member in accordance with the present disclosure;

FIG. 2 is a bottom plan view of the fastening member shown in FIG. 1;

FIG. 3 is perspective view of the fastening member shown in FIG. 1;

FIG. 4 is a perspective view of the fastening member shown in FIG. 1 illustrating one method of operation;

DETAILED DESCRIPTION OF PREFERRED EMBODIMENTS

Figure 5:
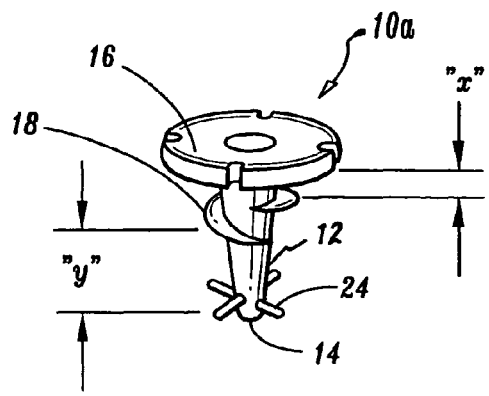
FIG. 5 is a perspective view of an alternate fastening member in accordance with the present disclosure.

Preferred embodiments of the presently disclosed fastening members are described in detail herein with reference to the drawing figures wherein like reference numerals identify similar or identical elements. In the drawings, and in the description which follows, the term "proximal", as is traditional, will refer to the end of the fastening member which is closest to the operator, while the term "distal" will refer to the end of the fastening member which is furthest from the operator.

Referring now in detail to the drawing figures and, in particular initially to FIGS. 1-4, a fastening member in the form of a surgical spiral conical tack is generally shown as 10. Tack 10 includes an elongated body portion 12 having an atraumatic, here shown as rounded, distal end 14 and a head 16 provided at a proximal end thereof. Preferably, head 16 has a diameter which is larger than a proximal end of body portion 12. Tack 10 includes a helical thread 18 commencing from distal end 14 and terminating at a distance "X" spaced from head 16. Head 16 is provided with at least one notch 20 formed along a rim 21 thereof. Notch 20 is preferably configured and dimensioned to be engaged by an engaging member such as a radially inwardly extending ridge 25 on the interior surface of a tubular shaft 27 of an applying tool 23 to assist in the rotation and application of tack 10 into a mesh material and underlying tissue. Head 16 also includes a stacking feature, here shown as a detent or recess 22 (see FIGS. 3 and 4) formed on a proximal surface of head 16 which is configured and adapted to receive therein a distal end 14 of another axially aligned adjacent tack 10 therein in a tip-to-tail configuration.

While tack 10 has been shown and described as having a rounded distal end 14, it is envisioned that distal end 14 of tack 10 can have any number of shapes, including and not limited to sharpened, conical, blunt, triad, helical/spiral or the like. Further, it is envisioned that while a body portion 12 is preferably conical, tack 10 can be formed having a tapered or substantially cylindrical body portion. In addition, body portion 12 can be provided with a longitudinal lumen or passage (not shown) which is co-axial with a longitudinal axis of tack 10. Preferably, body portion 12 of tack 10 is tapered such that body portion 12 has a girth which is smaller at distal end 14 than at the proximal end thereof.

An exemplary method of use of tack 10, in a hernia repair procedure, initially requires the use of conventional surgical techniques to prepare the hernia site within the patient's abdominal cavity and to place a conventional piece of biocompatible surgical mesh over the hernia site itself. A distal end of an applying tool, having at least one, usually a plurality of tacks 10 operatively associated with tool 23, is advanced into close proximity with and applied to the surface of the surgical mesh until helical thread 18 of a tack engages the surgical mesh. The applying tool is then used to rotate tack 10 which causes tack 10 to be drawn distally through the surgical mesh and into the tissue preferably until and so that the bottom surface of head 16 contacts the mesh. The process is repeated as many times as deemed necessary in order to secure the surgical mesh to the underlying tissue. For complete insertion of body portion 12 of tack 10 through the surgical mesh and into the body tissue it is preferred that helical thread 18 pass completely through the surgical mesh. If body portion 12 is inserted in that manner, tack 10 is prevented from coming free or backing out through the surgical mesh due to the abutment of the proximal end of helical thread 18 against the inner surface of the surgical mesh.

Turning now to FIG. 5, an alternative embodiment of a fastening member, in the form of a tack, is shown generally as 10a. In the present embodiment, helical thread 18 commences from a distance "Y" spaced from distal end 14 and terminates at a distance "X" spaced from head 16. According to the present embodiment, tack 10a is further provided with a plurality of radially extending resilient prongs 24 disposed between a distal end of helical thread 18 and distal end 14 of body portion 12. Preferably, resilient prongs 24 are capable of being deflected in proximal directions including in angular and arcuate or circumferential directions relative to elongated body portion 12. In use, tack 10a is inserted into the body tissue preferably by first pressing/pushing tack 10a distally and with little or no rotation through the surgical mesh, thereby deflecting resilient prongs 24 in a proximal direction, until helical thread 18 engages the surgical mesh. The applying tool is then used to rotate tack 10a which causes tack 10a to continue to move distally through the surgical mesh and into the tissue until the bottom surface of head 16 contacts the mesh. Upon rotation of tack 10a resilient prongs 24 deflect in angular and arcuate or circumferential directions relative to elongated body portion 12. In this embodiment, tack 10a is prevented from backing out due to the joint cooperation of helical thread 18 (as described above with regard to tack 10) and due to resilient prongs 24 (now at least partially oriented in a proximal direction) acting as anchors and that engage and are retained by the body tissue.

Figure 6:
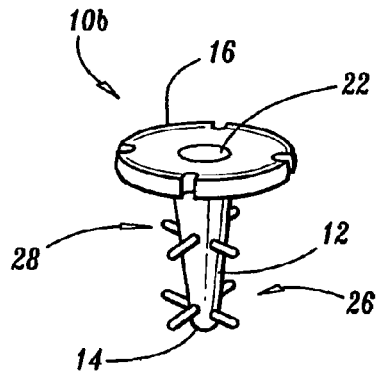
FIG. 6 is a perspective view of an alternate fastening member in accordance with the present disclosure.
Figure 7:
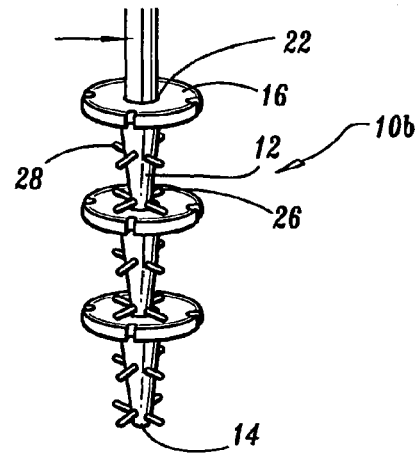
FIG. 7 is a perspective view of the fastening member of FIG. 6 in a stacked tip-to-tail orientation with other similar fastening members.
Figure 8:
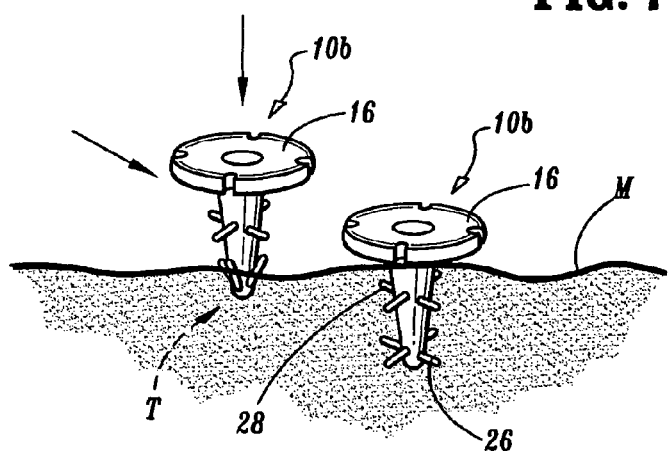
FIG. 8 is an illustration of the fastening member of FIG. 6 being inserted into mesh.

As seen in FIGS. 6-8, an alternative embodiment of a fastening member, in the form of a tack, is shown generally as 10b. Tack 10b includes a distal set of resilient prongs 26 extending radially from body portion 12 and a proximal set of resilient prongs 28 also extending radially from body portion 12. Preferably, distal prongs 26 are located proximate to and spaced a distance from distal end 14, while prongs 28 are located proximally of prongs 26 and, as here shown, spaced a distance from head 16. Prongs 26 and 28 are preferably capable of being deflected in a proximal direction, desirably toward head 16. Preferably, the prongs of a set are diametrically opposed to each other and axially aligned with the prongs of the other set.

In use, as seen in FIG. 8, as tack 10b is pressed through a surgical mesh "M", prongs 26 and 28 bend back (i.e., in a proximal direction) near or more preferably against body portion 12 allowing body portion 12 of tack 10b to pass through mesh "M". Once prongs 26 and 28 pass completely through mesh "M" and tack 10b is completely imbedded into underlying body tissue "T", preferably prongs 26 and 28 return to a substantially transverse orientation with respect to body portion 12, thus preventing tack 10b from being pulled back out through mesh "M". As seen in FIG. 7, a plurality of tacks 10b can be aligned and stacked in tip-to-tail fashion with one another by an engagement or placement of distal end 14 of body portion 12 in recess 22 formed in head 16. It is desirable to stack tacks of the disclosure in tip-to-tail fashion when a plurality of tacks are loaded directly into an applying tool or into a cartridge assembly which is later coupled to an insertion tool. Here, distal set of prongs 26 help to stabilize the upper tack relative to the underlying tack.

Figure 9:
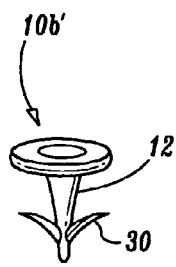
FIG. 9 is a perspective view of an alternate fastening member in accordance with the present disclosure.

FIG. 9 shows an alternative embodiment, a tack 10b', whose body portion 12 has a single pair of diametrically opposed resilient barbs 30. Barbs 30 are preferably oriented in a proximal direction wherein a distal end of each barb 30 is spaced a distance from body portion 12. Since barbs 30 are so oriented, insertion of tack 10b into body tissue is facilitated while removal of tack 10b from the body tissue is impeded by the anchoring effect of barbs 30 engaging into the body tissue.

While the shape of prongs 24, 26 and 28 have been shown throughout the figures as being substantially cylindrical in cross-section and having a certain length, it is envisioned that prongs 24, 26 and 28 can have a cross-sectional profile of any shape, including and not limited to, rectangular, triangular, polygonal, elliptical and the like. It is further envisioned that prongs 24, 26 and 28 can have any desired length as deemed necessary for the particular surgical procedure in which they are going to be used.

Figure 10:
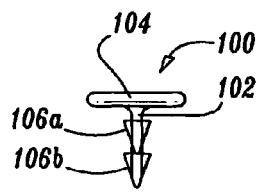
FIG. 10 is a side elevational view of an alternate fastening member in accordance with the present disclosure.
Figure 11:
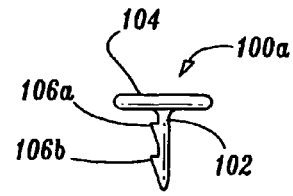
FIG. 11 is a side elevational view of an alternate fastening member in accordance with the present disclosure.
Figure 10A:
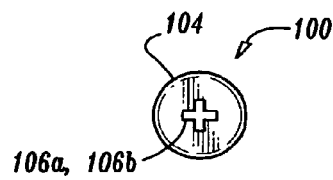
FIG. 10A is a bottom plan view of the fastening member shown in FIG. 10.
Figure 11A:
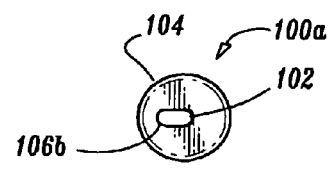
FIG. 11A is a bottom plan view of the fastening member shown in FIG. 11.

In FIGS. 10-11A, alternate embodiments of fastening members, in the form of tacks, are generally shown as 100. As seen in FIGS. 10 and 10A, tack 100 includes a head 104 and a body portion 102 having upper and lower sets of radially extending preferably rigid barbs 106a, 106b, extending radially from body portion 102. As shown, preferably the barbs of each pair are diametrically opposed, and the barbs of the pairs are axially aligned. In an alternative configuration, as seen in FIGS. 11-11A, tack 100a is provided with a single upper barb 106a and a single lower barb 106b. Barbs 106a, 106b are formed along one side of leg 102. It is envisioned that any number of barbs 106 can be provided along the outer surface of leg 102. Moreover, barbs 106 can be oriented in any radial direction relative to one another.

Figure 12:
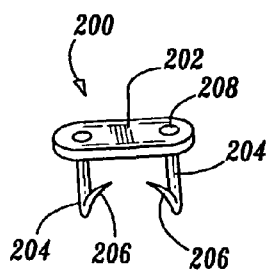
FIG. 12 is a perspective view of an alternate fastening member in accordance with the present disclosure.
Figure 13:
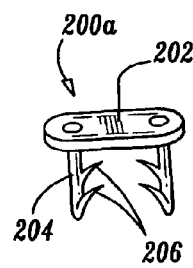
FIG. 13 is a perspective view of an alternate fastening member in accordance with the present disclosure
Figure 14:
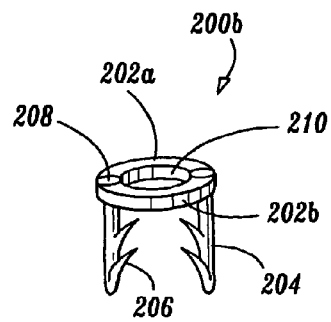
FIG. 14 is a perspective view of an alternate fastening member in accordance with the present disclosure.

Turning now to FIGS. 12-14, an alternative fastening member, here shown in the form of a tack generally depicted 200. As seen in FIG. 12, tack 200 includes an elongated backing member 202 having a leg 204 depending from each end thereof. Preferably, each leg 204 is substantially orthogonal with respect to an axis defined by backing member 202. Legs 204 are preferably substantially oriented in the same direction as one another. Each leg 204 is provided with a substantially oriented resilient barb 206 formed at a distal end thereof. Preferably, the terminal end of each barb 206 is spaced from the leg 204 from which it extends. While, as seen in FIG. 12, it is preferred that barbs of the tacks of the disclosure, for example, here 206, are directed or generally oriented toward one another, it is envisioned that barbs 206 can be disposed in any radial and/or proximal direction anywhere about each leg 204. Backing member 202 preferably is provided with a pair of recesses 208 formed in a proximal surface thereof. Preferably, recesses 208 are axially aligned with a longitudinal axis of a respective leg 204 and are configured and adapted to receive the distal ends of respective legs 204 from an adjacent tack 200. In an alternative embodiment, shown in FIG. 13, each leg 204 of tack 200 includes a pair of barbs 206. Preferably, barbs 206 of each leg 204 are oriented directly or generally towards each other.

In yet another embodiment, shown in FIG. 14, tack 200b includes a backing member 202 that is annular and is defined by a single, a pair or by a plurality of arcuate backing members 202a and 202b. Annular backing-member 202 defines an opening 210 therethrough which can be for receiving a shaft of an insertion tool therethrough. Backing-member 202 further includes a pair of recesses 208 formed in a proximal surface thereof, which recesses 208 are axially aligned with a longitudinal axis of a respective leg 204. The recess(es) in the backing member(s) of the tacks of the disclosure can be configured for stacking and/or application purposes.

Figure 15:
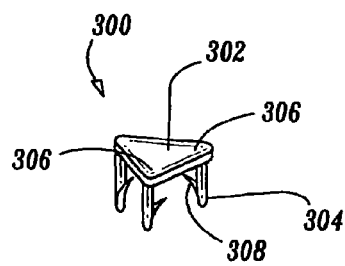
FIG. 15 is a perspective view of an alternate fastening member in accordance with the present disclosure.

FIG. 15 shows an alternative embodiment of a fastening member, in the form of a tack, generally shown as 300. Tack 300 includes a triangular head 302 having a leg 304 depending from each corner 306 thereof. Each leg 304 is provided with at least one barb 308 formed on and preferably along a portion of the length thereof, preferably, at or near a distal tip thereof. It is envisioned that barbs 308 are oriented in a direction facing substantially toward a center of head portion 302.

An exemplary method of use of the tacks disclosed herein (hereinafter, for simplicity, "tack 100") in a hernia repair procedure will now be described. The hernia site in the patient's abdominal cavity is first prepared using conventional surgical techniques and a conventional piece of biocompatible surgical mesh is placed over the hernia site, understood to include tissue or body portions surrounding the hernia. Next, tack 100 is applied by a tack applier, or by grasping tack 100 with an appropriate grasping instrument and placing the tack into position proximate to the tissue to be fastened. Preferably, the tack is positioned such that the legs are oriented substantially perpendicular to the surface of the tissue. Tack 100 is then pushed distally until its distal ends penetrate the mesh and the underlying tissue, preferably until the distal surface of the head contacts the surface of the surgical mesh. The procedure is repeated as many times with as many tacks as deemed necessary to secure the mesh to the underlying tissue.

Although this disclosure has been shown and described with respect to detailed embodiments thereof, it will be understood by those skilled in the art that various changes in form and detail thereof may be made without departing from the spirit and scope of the disclosure.

For example, preferably, the head of each fastening member is flattened to reduce interference with or reduce trauma to the body. While a flattened head is preferred, it is contemplated that the head can take on any configuration, including and not limited to arcuate, hemispherical, rectangular or the like.

The fastening members of the present disclosure may be manufactured from biocompatible absorbable or non-absorbable (i.e., stainless steel, titanium, polymers, composites and the like and equivalent) materials. It is particularly preferred that the fastening members of the present disclosure are manufactured from absorbable materials which are absorbed into the body over the course of the healing process thereby eliminating the existence of the fastener after it is no longer needed to perform its function of approximating or fastening tissue or body matter. Examples of absorbable materials include homopolymers and copolymers of lactide, glycolide, trimethylene carbonate, caprolactone, and p-dioxanone and blends thereof.

From the foregoing, it will be observed that numerous variations and modifications may be effected without departing from the true spirit and scope of the novel concepts of the disclosure. Further, it is to be understood that no limitation with respect to the specific articles, instruments and methods disclosed herein is intended or should be inferred.

What is claimed is:

1. A tack for use during a surgical procedure and in an instrument that is configured to retain a plurality of tacks stacked in tip to tail fashion, the tack comprising:
    a circular head having a proximal surface and a distal surface;
    an elongate body portion extending from the distal surface of the circular head, the elongate body portion having proximal and distal ends;
    a plurality of anchoring elements extending radially from an outer surface of the elongate body portion for inhibiting the removal of the tack from body tissue, the plurality of anchoring elements consisting of:
    a single proximal anchoring element;
    a single distal anchoring element disposed on a single side of a distal-most end of the elongate body portion and distal of the single proximal anchoring element; and
    wherein the proximal surface of the circular head defines a recess having a shape complementary to the single distal anchoring element.

2. The tack according to claim 1, wherein at least one anchoring element of the plurality of anchoring elements is a barb.

3. The tack according to claim 1, wherein the plurality of anchoring elements is sharpened.

4. The tack according to claim 1, wherein the elongated body portion defines a longitudinal axis extending between the proximal and distal ends thereof, the distal-most end of the elongated body portion defined along an imaginary plane extending perpendicular to the longitudinal axis of the elongated body portion.

* * * * *